United States Patent [19]
Verkaart et al.

[11] Patent Number: 5,707,431
[45] Date of Patent: Jan. 13, 1998

[54] VORTEX GAS ELIMINATION DEVICE

[75] Inventors: Wesley H. Verkaart; Christina J. Sundstrom, both of Duxbury; James R. Ellsworth, Mashpee, all of Mass.

[73] Assignee: SIMS Level 1, Inc., Rockland, Mass.

[21] Appl. No.: 767,199

[22] Filed: Dec. 18, 1996

Related U.S. Application Data

[63] Continuation of Ser. No. 322,992, Oct. 14, 1994, abandoned, which is a continuation-in-part of Ser. No. 196,760, Feb. 15, 1994, abandoned.

[51] Int. Cl.$^6$ ............................................. B01D 19/00
[52] U.S. Cl. ............................. 96/177; 55/337; 55/417; 55/482; 55/498; 96/209; 96/219; 210/430; 210/436; 210/512.1
[58] Field of Search ........................... 55/320, 327, 337, 55/417, 459.1, 482, 498, 502; 96/177, 209, 212, 216, 219; 210/349, 430, 436, 453, 472, 512.1; 422/101

[56] References Cited

U.S. PATENT DOCUMENTS

| | | | |
|---|---|---|---|
| 2,784,733 | 3/1957 | Martinez . | |
| 2,879,784 | 3/1959 | Cutter | 137/192 |
| 3,105,511 | 10/1963 | Murphy | 137/399 |
| 3,276,188 | 10/1966 | Carlson | 96/212 |
| 3,476,251 | 11/1969 | Kudlaty | 210/436 |
| 3,616,802 | 11/1971 | Marinaccio | 55/417 |
| 3,771,290 | 11/1973 | Stethem | 210/512.1 |
| 3,834,126 | 9/1974 | Diminno, Jr. | 55/327 |
| 3,993,062 | 11/1976 | Jess | 128/214 R |
| 4,004,587 | 1/1977 | Jess | 128/214 R |
| 4,013,072 | 3/1977 | Jess | 128/214 R |
| 4,028,254 | 6/1977 | Shufflebarger et al. | 55/498 |
| 4,365,980 | 12/1982 | Culbert et al. | 55/498 |
| 4,411,783 | 10/1983 | Dickens et al. | 210/304 |
| 4,572,724 | 2/1986 | Rosenberg et al. | 210/436 |
| 4,662,906 | 5/1987 | Matkovich et al. | 55/318 |
| 4,690,762 | 9/1987 | Katsura | 210/436 |
| 4,758,337 | 7/1988 | Kohn et al. | 96/219 |
| 4,806,135 | 2/1989 | Siposs | 55/204 |
| 4,870,987 | 10/1989 | Cheng | 137/192 |
| 4,900,308 | 2/1990 | Verkaart | 604/126 |
| 4,919,802 | 4/1990 | Katsura | 210/188 |
| 4,932,987 | 6/1990 | Molina | 55/487 |

FOREIGN PATENT DOCUMENTS 3837 896   5/1990   Germany .

*Primary Examiner*—C. Scott Bushey
*Attorney, Agent, or Firm*—Dickinson, Wright, Moon, Van Dusen & Freeman

[57] ABSTRACT

A gas elimination device for cellular fluids has a cylindrical chamber that is divided radially into two parts by a cylindrical filter centrally located in the chamber. The fluid inlet is directed tangentially to the outer part of the chamber to create a vortex flow. The vortex flow is stopped by passage of the fluid through the filter, and gas bubbles that have formed rise to the top of the outer part of the chamber. A hydrophobic membrane covers the top of the chamber and allows the gas to exit the chamber to the atmosphere. A one way valve formed in a two part cap covering the chamber prevents flow of air into the chamber. A float valve stops flow when the chamber fills with air.

13 Claims, 1 Drawing Sheet

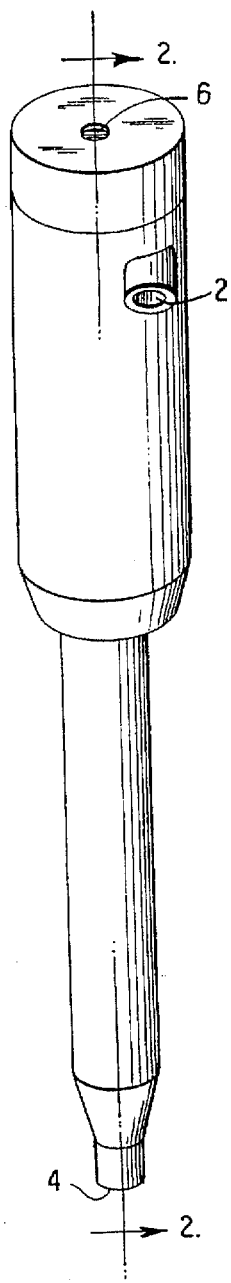
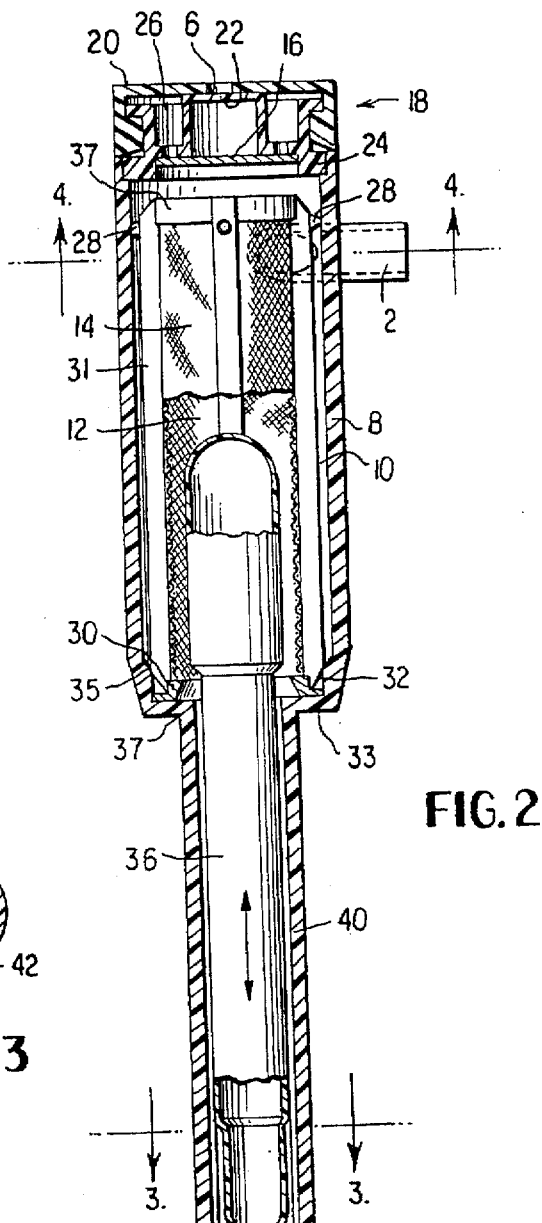
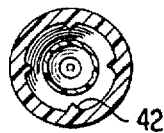
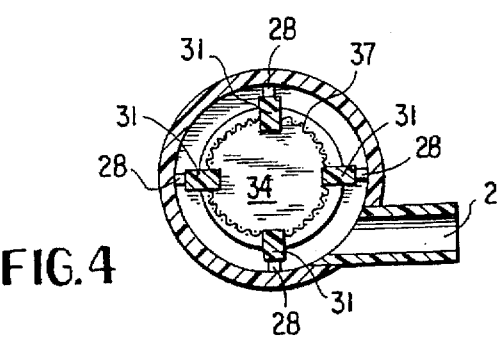
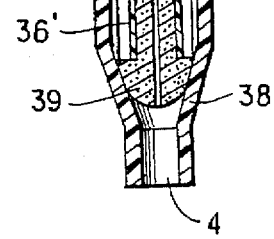
FIG. 1
FIG. 2
FIG. 3
FIG. 4

VORTEX GAS ELIMINATION DEVICE

This is a continuation of U.S. application Ser. No. 08/322,992 (filed Oct. 14, 1994), now abandoned, which is a continuation in part of Ser. No. 08/196,760 (filed Feb. 15, 1994) now abandoned.

FIELD OF THE INVENTION

This invention relates to the art of filters for physiological fluids, particularly cellular fluids.

BACKGROUND

When administrating physiological fluids to a patient, it is necessary to ensure that all foreign particles and gas bubbles are removed, as these may prove dangerous to the patient. Accordingly it is known to pass these fluids through a filter prior to their admission to the patient.

One known filter is shown in a prior United States patent of one of the applicants herein, U.S. Pat. No. 4,900,308. The filter shown in that patent provides a plenum that is sufficiently large that the downward velocity of the fluid is less that the upward velocity of gas bubbles that form in the fluid. Thus, the gas rises to the top of the plenum. A hydrophobic membrane covers the top of the plenum, and the gas separated from the fluid exits to the atmosphere through this membrane. This structure has been found very useful for cellular fluids because it relies on natural separation of the gas from the fluid and not on such elements as hydrophilic membranes.

Another prior filter is shown in U.S. Pat. No. 4,662,906. That filter includes structure that first separates gas from fluid by introducing a vortex flow into the fluid. Gas bubbles that become separated from the fluid move to the inner part of the vortex and into a chamber formed, in part, by a hydrophobic membrane. The gas exits to the atmosphere through this membrane. The fluid, which may have additional gas that has not been separated, is passed through a defoaming sponge that has been treated with an antifoaming agent. The sponge causes additional gas bubbles to form and separate from the fluid. The fluid and gas bubbles exit from the sponge material into a cylindrical element located within a storage reservoir. When the fluid and bubbles pass out of the cylindrical element, the gas is allowed to rise to the chamber and the gas is allowed to pass through the hydrophobic membrane to the atmosphere.

SUMMARY OF THE INVENTION

In accordance with the invention, a gas separation and filter device for a physiological fluid, such as blood, includes a cylindrical chamber that is divided radially into two portions by a cylindrical filter. The chamber has an inlet for introducing the fluid tangentially with respect to the axis of the chamber to form a vortex in the outer portion of the chamber. The centrifugal action of the vortex separates gas bubbles that arise, for example, through heating of the fluid, from the remainder of the fluid. These bubbles are allowed to rise to the top of the chamber, either through the fluid freely or by coalescing on the filter and then rising. The top of the chamber is covered with a hydrophobic membrane, which allows the gas that has separated from the fluid and risen to the top of the chamber to escape to the atmosphere. A one-way valve that prevents reverse flow through the hydrophobic membrane is flexible and provides an audible "squeal" when air is being vented from the chamber to indicate that gas is present in the fluid and is being vented.

The filter that separates the inner portion of the chamber from the outer portion stops the vortex motion and removes additional contaminants from the fluid as the fluid passes through it.

The filtered fluid flows downward through the inner portion of the chamber to an outlet. The outlet is controlled by a float valve that terminates flow through the device when the fluid level in the chamber is inadequate.

This construction provides improved separation of gas bubbles and a larger hydrophobic membrane. Thus, the filter is capable of removing air or other gasses at higher flow rates.

BRIEF DESCRIPTION OF THE DRAWINGS

FIG. 1 is a perspective of a gas elimination device in accordance with the invention. The device of the invention is illustrated to scale in the drawing figures.

FIG. 2 is a cross section taken along line 2—2 of FIG. 1.

FIG. 3 is a cross section taken along line 3—3 of FIG. 2.

FIG. 4 is a cross section taken along line 4—4 of FIG. 2.

DETAILED DESCRIPTION OF THE PREFERRED EMBODIMENT

FIG. 1 is a perspective of a preferred embodiment of a gas elimination device in accordance with the invention. The device includes a fluid inlet 2, a fluid outlet 4, and a gas outlet 6.

FIG. 2 shows the construction of the device of FIG. 1 in detail. Fluid is supplied through inlet 2 to a generally cylindrical plenum chamber 8. The chamber is divided into an outer portion 10 and an inner portion 12 by a generally cylindrical filter 14. As the fluid enters the outer portion 10 of the chamber 8, a vortex motion is imparted to the fluid because the inlet is directed into the chamber in a tangential direction, as shown more clearly in FIG. 4. This vortex motion causes the gas contained in the fluid to separate from the fluid and rise to the top of the outer portion. The separation of the gas bubbles is caused by both the centrifugal forces in the vortex and the buoyancy of the bubbles. Preferably, the chamber is sized such that the downward velocity of the fluid is less than the upward velocity of a bubble with respect to the fluid as described in U.S. Pat. No. 4,900,308, mentioned above.

The gas bubbles that do not rise freely in the fluid tend to coalesce on the outer surface of the filter 14 and then rise when they are detached from the filter by interaction with the fluid.

The fluid then passes from the outer portion through the filter 14 into the inner portion. In addition to removing foreign particulate matter from the fluid as it passes through, filter 14 also acts as a baffle to stop the vortex motion of the fluid. The filter is closed at its top, whereby the fluid must exit through the bottom of the inner portion of the chamber.

The top of the chamber 8 is covered with a hydrophobic membrane 16, which is mounted in a two-part cap 18. The two-part cap 18 covers the chamber and provides a one-way valve made of a flexible upper surface 20 having gas outlet 6 therein and a seat 22. In the normal situation, gas passing through membrane 16 generates enough pressure to lift upper surface 20 from seat 22 to allow the gas to exit the device. When the pressure in the device is at or lower than atmospheric pressure, however, the upper surface 20 is pushed against the seat 22 to prevent the flow of air into the device.

Seat 22 is preferably integral with structure 24, which also supports the membrane 16 and includes holes 26 for allowing the air to flow upward and press against the surface 20. Structure 24 and upper surface 20 may be made of different materials to provide the necessary flexibility in the upper surface and rigidity of the structure 24. The structure 24 is preferably made of acrylic, but may be made of other materials including polycarbonate, ABS, polyester or styrene. The flexible material is preferably made of thermoplastic elastomer (TPE), one suitable material being that sold under the trademark "Krayton." As well, the flexible material may be made of such materials as latex, thermoplastic rubber (TPR) or silicone. Because the upper surface is flexible, exiting gas causes it to emit an audible "squeal", which indicates to the medical personnel that the device is operating to remove gas from the fluid.

Chamber 8 and filter 14 are designed for ease of assembly. The upper end of the filter 14 includes fingers 28 that hold the top of the filter away from the sides of the chamber. As seen in FIG. 4, these fingers are spaced about the circumference of the filter to provide room for the rising bubbles to pass to the membrane 16. A seal 30 is located at the lower end of the filter 14 to prevent leakage between the bottom of the filter and the chamber. The engagement between the side of the chamber and the seal 30 is an interference fit, it being unnecessary to bond the filter to the chamber. The diameter of lower seal 30 is smaller than the diameter of fingers 28 to allow the filter to be easily installed in the chamber, the smaller diameter seal moving freely to the bottom of chamber 8 during installation until it engages a narrowed part to form a liquid tight seal. In the embodiment shown in FIG. 2, the narrowed part of the chamber comprises a cylindrical section 32 that is perpendicular to base 33. The upper part of section 32 is connected to the larger cylinder by a conical section 35.

The vertical position of filter 14 may vary by a distance equal to the length of the reduced diameter portion 32. Thus, the primary requirement is that the filter be located far enough into the chamber such that the lower seal 30 engages the reduced diameter portion 32 of the chamber. This feature contributes to ease of manufacture of the device.

The structure 24 is preferably welded ultrasonically to the chamber 8. Then, the more flexible outer covering that includes surface 20 is then snapped over the structure 24 and is held in place by the resiliency of the material without additional bonding.

As shown in FIG. 4, the filter is closed by a top 34. The filter itself includes a plurality of ribs 31 that extend between upper and lower rings 37. The filter material is sealed to the ribs and rings, for example, by ultrasonic welding or insert molding.

Outlet 4 includes a shut off valve comprising a float 36 and a tapered section 38 that engages the bottom of the float when inadequate fluid is present in the device. The float 36 is preferably elongate, a first part being concentric with an elongate section 40 of the device directly below the inner portion of the chamber 8 and a second part being within the inner portion 12. The elongate profile results in increased buoyancy of the float, and the height of the float in a preferred embodiment is about five inches.

While the float is generally blow-molded of plastic, the end 39 is preferably made of a resilient silicone material, which provides a very effective seal when the tip of the float engages the tapered portion 38 to prevent the flow of air to a patient line (not shown) attached to outlet 4. The float may also be entirely one hollow plastic component or one piece of other plastic. A tip 36' of the float is preferably formed into a bell-jar shape to accommodate a nipple on the end 39 to allow it to be inserted easily into the blow molded part.

As shown in FIG. 3, the elongate section 40 includes inward directed ribs 42 for maintaining a space between the float and the sides of section 40 to prevent attachment between the float and the section 40 caused by surface tension.

It will be appreciated that a unique air elimination filter has been described. The gas removal function is effected by a vortex flow, which causes much of the gas to be separated by centrifugal forces, and by allowing gas bubbles to rise naturally. Modifications within the scope of the appended claims will be apparent to those of skill in the art.

We claim:

1. Apparatus for separating a gas from a fluid comprising a housing forming an elongate chamber, dividing means comprising a filter pervious to said fluid and said gas for dividing said chamber radially into outer and inner portions, inlet means for directing said fluid into said outer portion and for forming a vortex in said fluid in said outer portion, means for venting from said chamber gas that has been separated from said fluid, and outlet means for discharging said fluid from said inner portion wherein said outlet means comprises an elongate section having a fluid outlet and a float movable vertically in said elongate section for closing said outlet when said elongate section contains a predetermined amount of gas.

2. Apparatus according to claim 1 wherein said dividing means is positioned such that said fluid flows from said outer portion through said dividing means and into said inner portion and said dividing means substantially terminates vortex flow in said fluid.

3. Apparatus according to claim 1 wherein said means for venting comprises a hydrophobic membrane.

4. Apparatus according to claim 1 wherein said float comprises a tip that engages said fluid outlet to stop flow of said gas.

5. Apparatus according to claim 1 wherein said chamber comprises an upper cylindrical part aligned with said elongate section.

6. Apparatus according to claim 2 wherein said means for venting comprises one-way valve means for preventing the drawing of air into said chamber, said one-way valve means comprising a first part forming a valve seat and a second part made of flexible material and covering said seat, said second part having an outlet opening therein.

7. Apparatus for separating gas from a fluid comprising a housing forming a chamber, a filter extending axially along said chamber to divide said chamber radially into inner and outer portions, an inlet for supplying said fluid to the outer portion of said chamber and for forming a vortex in said fluid in said outer portion, means for supporting a hydrophobic membrane in communication with said chamber for allowing gas separated from said fluid to exit said apparatus, wherein said filter substantially stops vortex flow in said fluid as said fluid flows through said filter, and the downward velocity of fluid in said chamber is slower than the upward velocity of gas bubbles, whereby gas bubbles form in said fluid and gas exits through said hydrophobic membrane and further comprising outlet means for allowing said fluid to exit said chamber, said outlet means comprising an elongate section having a fluid outlet and a float movable vertically in said elongate section for closing said outlet when said elongate section contains a predetermined amount of gas.

8. Apparatus according to claim 7, wherein said filter includes separating means near the inlet for separating the filter from the sides of the chamber and sealing means for engaging an end portion of said chamber remote from said inlet and the transverse dimension of said seal is smaller than the transverse dimension of said separating means to facilitate insertion of said filter into said chamber.

9. Apparatus according to claim 8 wherein said chamber is cylindrical.

10. Apparatus for separating gas from a fluid comprising a housing forming a chamber, a filter extending axially along said chamber to divide said chamber radially into inner and outer portions, an inlet for supplying said fluid to the outer portion of said chamber and for forming a vortex in said fluid in said outer portion, means for supporting a hydrophobic membrane in communication with said chamber for allowing gas separated from said fluid to exit said apparatus, wherein said filter substantially stops vortex flow in said fluid as said fluid flows through said filter, and the downward velocity of fluid in said chamber is slower than the upward velocity of gas bubbles, whereby gas bubbles form in said fluid and gas exits through said hydrophobic membrane, wherein said means for supporting a hydrophobic membrane comprises a first part forming a valve seat and a second part made of flexible material covering said valve seat for engaging and sealing said valve seat, and wherein said second part comprises an outlet opening therein aligned with said valve seat for discharging gas that has passed through said hydrophobic membrane when said second part is displaced from said valve seat.

11. Apparatus according to claim 10 wherein said first and second parts form a one-way valve for allowing discharge of said gas when the pressure of said gas that has passed said hydrophobic membrane is greater than atmospheric pressure and preventing ingress of air when said pressure of said gas that has passed said hydrophobic membrane is less than atmospheric pressure.

12. Apparatus according to claim 11 wherein said second part is lifted from said seat to allow discharge of said gas when the pressure of said gas that has passed said hydrophobic membrane is greater than atmospheric pressure and said second part is held against said seat to prevent ingress of air when said pressure of said gas that has passed said hydrophobic membrane is less than atmospheric pressure.

13. Apparatus according to claim 12 wherein said first part comprises a relatively rigid structure having said hydrophobic membrane attached to a lower surface thereof, said valve seat extends upward from said lower surface, and said lower surface includes means surrounding said valve seat for allowing passage of said gas that has passed through said membrane to said valve seat.

* * * * *